(12) United States Patent
Singleton et al.

(10) Patent No.: US 9,060,511 B2
(45) Date of Patent: Jun. 23, 2015

(54) COMPOSITIONS OF DIBROMOMALANOMIDE AND THEIR USE AS BIOCIDES

(75) Inventors: Freddie L. Singleton, Vernon Hills, IL (US); Tirthankar Ghosh, Oreland, PA (US); Kimberly S. Cagle, Schaumburg, IL (US)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 179 days.

(21) Appl. No.: 13/814,525

(22) PCT Filed: Aug. 3, 2011

(86) PCT No.: PCT/US2011/046346
§ 371 (c)(1),
(2), (4) Date: Feb. 6, 2013

(87) PCT Pub. No.: WO2012/021340
PCT Pub. Date: Feb. 16, 2012

(65) Prior Publication Data
US 2013/0142886 A1 Jun. 6, 2013

Related U.S. Application Data

(60) Provisional application No. 61/371,906, filed on Aug. 9, 2010.

(51) Int. Cl.
| A01N 59/00 | (2006.01) |
| A01N 37/18 | (2006.01) |
| A01N 59/20 | (2006.01) |
| A01N 37/30 | (2006.01) |
| C02F 103/02 | (2006.01) |
| C02F 1/50 | (2006.01) |

(52) U.S. Cl.
CPC .............. *A01N 37/18* (2013.01); *A01N 59/00* (2013.01); *A01N 37/30* (2013.01); *A01N 59/20* (2013.01); *C02F 1/50* (2013.01); *C02F 2103/023* (2013.01); *C02F 2303/08* (2013.01)

(58) Field of Classification Search
None
See application file for complete search history.

(56) References Cited

U.S. PATENT DOCUMENTS

| 3,092,552 | A | * | 6/1963 | Romans ..................... 424/404 |
| 4,163,795 | A | | 8/1979 | Burk |
| 4,608,183 | A | | 8/1986 | Rossmoore |
| 4,800,082 | A | | 1/1989 | Karbowski et al. |
| 5,662,913 | A | * | 9/1997 | Capelli ..................... 424/405 |
| 5,922,745 | A | * | 7/1999 | McCarthy et al. .......... 514/372 |
| 2004/0261196 | A1 | | 12/2004 | Ghosh et al. |
| 2005/0132946 | A1 | | 6/2005 | Maurer et al. |
| 2008/0112920 | A1 | | 5/2008 | Chia et al. |
| 2008/0227766 | A1 | | 9/2008 | Wunder et al. |
| 2010/0015245 | A1 | | 1/2010 | Harrison et al. |

FOREIGN PATENT DOCUMENTS

| GB | 2353522 A | * | 2/2001 |
| WO | WO 2008091453 A1 | * | 7/2008 |

OTHER PUBLICATIONS

Podbudnaya et al. Zhurnal Obsshchei Khimii 1948 18:1848; abstract only.*

* cited by examiner

Primary Examiner — Juliet Switzer
Assistant Examiner — Caralynne Helm
(74) Attorney, Agent, or Firm — Tifani M. Edwards

(57) ABSTRACT

A biocidal composition comprising 2,2-dibromomalonamide and a metal selected from silver, copper, and mixtures thereof, and its use for the control of microorganisms in aqueous and water-containing systems.

9 Claims, No Drawings

COMPOSITIONS OF DIBROMOMALANOMIDE AND THEIR USE AS BIOCIDES

CROSS-REFERENCE TO RELATED APPLICATION(S)

This application claims the benefit of priority from U.S. Provisional Patent Application No. 61/371,906, filed Aug. 9, 2010, which application is incorporated by reference herein in its entirety

FIELD OF THE INVENTION

The invention relates to biocidal compositions and methods of their use for the control of microorganisms in aqueous and water-containing systems. The compositions comprise 2,2-dibromomalonamide and a metal selected from silver, copper, and mixtures thereof.

BACKGROUND OF THE INVENTION

Water systems provide fertile breeding grounds for algae, bacteria, viruses, and fungi some of which can be pathogenic. Such microorganism contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that provide one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition is useful for controlling microorganisms in aqueous or water containing systems. The composition comprises: 2,2-dibromomalonamide and a metal selected from silver, copper, and mixtures thereof.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: 2,2-dibromomalonamide and a metal selected from silver, copper, and mixtures thereof. It has surprisingly been discovered that combinations of 2,2-dibromomalonamide and the metal as described herein, at certain weight ratios, are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation. In some preferred embodiments, "control" and "controlling" mean inhibiting the growth or propagation of microorganisms. In further embodiments, "control" and "controlling" mean the killing of microorganisms.

The terms "2,2-dibromomalonamide," "dibromomalonamide," and "DBMAL" mean a compound represented by the following formula:

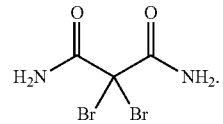

In some embodiments of the invention, the weight ratio of 2,2-dibromomalonamide to the metal is between about 1000:1 and about 1:100, alternatively between about 800:1 and about 1:1. The 2,2-dibromomalonamide is commercially available and/or may be readily prepared by those skilled in the art using well known techniques.

In some embodiment, the composition of the invention comprises 2,2-dibromomalonamide and silver. The silver may be in any ionic or non-ionic form that is capable of reacting with a cellular component of a microorganism. The silver is preferably obtained from an inorganic or organic source or by electrolytic generation of silver ions. Examples include, but are not limited to one or more of the following: silver acetate, silver acetylacetonate, silver arsenate, silver benzoate, silver bromate, silver bromide, silver carbonate, silver chlorate, silver chloride, silver chromate, silver citrate hydrate, silver cyanate, silver cyclohexanebutyrate, silver fluoride, silver heptafluorobutyrate, silver hexafluoroantimonate, silver hexafluoroarsenate, silver hexafluorophosphate, silver hydrogen fluoride, silver iodate, silver iodide, silver lactate, silver metavanadate, silver methanesulfonate, silver methenamine, silver molybdate, silver nitrate, silver nitrite, silver oxide, silver pentafluoropropionate, silver perchlorate hydrate, silver perchlorate monohydrate, silver perchlorate, silver phosphate, silver phthalocyanine, silver picolinate, silver protein, silver proteinate, silver p-toluenesulfonate, silver selenide, silver sulfadiazine, silver sulfate, silver sulfide, silver sulfite, silver telluride, silver tetrafluoroborate, silver thiocyanate, silver trifluoroacetate, silver trifluoromethanesulfonate, or silver tungstate. A preferred source is silver nitrate. The silver can also be obtained from a formulation designed to control the release of silver. Examples of controlled release formulations of silver include those based on organic polymers, zeolites, glass, calcium phosphate, titanium dioxide and zinc oxide. These formulations can employ the various inorganic or organic silver forms mentioned above.

In some embodiments, the weight ratio of 2,2-dibromomalonamide to silver is between about 800:1 and about 1:1, alternatively between about between about 800:1 and about 6:1, alternatively between about 800:1 and about 12.5:1, or alternatively between about 400:1 and about 6:1.

In some embodiment, the composition of the invention comprises 2,2 dibromomalonamide and copper. The copper may be in any ionic or non-ionic form that is capable of reacting with a cellular component of a microorganism. The copper is preferably obtained from an inorganic or organic source or by electrolytic generation of copper ions. Examples include, but are not limited to one or more of the following: copper acetate; copper acetylacetonate; copper bromide; copper carbonate; copper chloride; copper chromite; copper cyanide; copper cyclohexanebutyrate; copper D-gluconate; copper fluoride; copper formate hydrate; copper hexafluoroacetylacetonate hydrate; copper hydroxide; copper iodide; copper iodide dimethyl sulfide complex; copper iodide trimethylphosphite complex; copper methoxide; copper molybdate; copper nitrate; copper oxide; copper oxychloride; copper perchlorate hexahydrate; copper pyrophosphate hydrate; copper selenide; copper selenite; copper sulfate; copper sulfide; copper tartrate hydrate; copper telluride; copper thiocyanate; copper thiophene-2-carboxylate; copper thiophenolate; copper trifluoroacetylacetonate; copper 1-butanethiolate; copper 2-ethylhexanoate; copper 3-methylsalicylate; or copper trifluoromethanesulfonate. A preferred source is copper sulfate. The copper can also be obtained from a formulation designed to control the release of copper. Examples of controlled release formulations of copper include those based on organic polymers, zeolites, glass, calcium phosphate, titanium dioxide and zinc oxide. These formulations can employ the various inorganic or organic copper forms mentioned above.

In some embodiments, the weight ratio of 2,2-dibromomalonamide to copper is between about 100:1 and about 1:1, alternatively between about 70:1 and about 1:1, alternatively about 40:1 and about 1:1, alternatively between about 32:1 and about 1:1, or alternatively between about 16:1 and 1:1 or 16:1 and 2:1.

The foregoing ratios are based on the amount of the metal in the composition, even though the metal may have been delivered, e.g., as an inorganic or organic compound.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oilfield water, pulp and paper water, cooling water), oilfield functional fluids such as drilling muds and fracturing fluids, fuels, air washers, wastewater, ballast water, filtration systems, and swimming pool and spa water. Preferred aqueous systems are metal working fluids, personal care, household and industrial cleaners, industrial process water, and paints and coatings. Particularly preferred are industrial process water, paints and coatings, metal working fluids, and textile fluids such as spin finishes.

A person of ordinary skill in the art can readily determine, without undue experimentation, the effective amount of the composition that should be used in any particular application to provide microorganism control. By way of illustration, a suitable actives concentration (total for both 2,2-dibromomalonamide and metal) is typically at least about 0.001 weight percent, alternatively at least about 0.01 weight percent, based on the total weight of the aqueous or water containing system including the biocide composition.

In some embodiments, a suitable upper limit for the actives concentration is about 5 weight percent or less, alternatively 1 weight percent, or alternatively 0.1 weight percent, based on the total weight of the aqueous or water containing system.

The components of the composition may be added to the aqueous or water containing system separately, or preblended prior to addition. A person of ordinary skill in the art can easily determine the appropriate method of addition. The composition may be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

The results provided in the Examples are generated using a growth inhibition assay. Details of each assay are provided below.

Growth Inhibition Assay. The growth inhibition assay used in the Examples measures inhibition of growth (or lack thereof) of a microbial consortium Inhibition of growth can be the result of killing of the cells (so no growth occurs), killing of a significant portion of the populations of cells so that regrowth requires a prolonged time, or inhibition of growth without killing (stasis). Regardless of the mechanism of action, the impact of a biocide (or combination of biocides) can be measured over time on the basis of an increase in the size of the community.

The assay measures the efficacy of one or more biocides at preventing growth of a consortium of bacteria in a dilute mineral salts medium. The medium contains (in mg/l) the following components: $FeCl_3.6H_2O$ (1); $CaCl_2.2H_2O$ (10); $MgSO_4.7H_2O$ (22.5); $(NH_4)_2SO_4$ (40); $KH_2PO_4$ (10); $K_2HPO_4$ (25.5); Yeast Extract (10); and glucose (100). After all components are added to deionized water, the pH of the medium is adjusted to 7.5. Following filter sterilization, aliquots are dispensed in 100 µl quantities to sterile microtiter plate wells. Dilutions of 2,2-dibromomalonamide ("DBMAL") and/or "Biocide B" are then added to the microtiter plate. After preparing the combinations of actives as illustrated below, each well is inoculated with 100 µl of a cell suspension containing ca. $1 \times 10^6$ cells per milliliter of a mixture of *Pseudomonas aeruginosa, Klebsiella pneumoniae, Staphylococcus aureus*, and *Bacillus subtilis*. The final total volume of medium in each well is 300 µl. Once prepared as described herein, the concentration of each active ranged from 25 ppm to 0.195 ppm as illustrated in Table 1. The resulting matrix allows testing of eight concentrations of each active and 64 combinations of actives in the ratios (of actives).

TABLE 1

Template for microtiter plate-based synergy assay showing concentrations of each active. Ratios are based on weight (ppm) of each active.

| | | DBMAL (ppm) | | | | | | | |
|---|---|---|---|---|---|---|---|---|---|
| | | 25 | 12.5 | 6.25 | 3.125 | 1.563 | 0.781 | 0.391 | 0.195 |
| Biocide B (ppm) | 25 | 1:1 | 1:2 | 1:4 | 1:8 | 1:16 | 1:32 | 1:64 | 1:128 |
| | 12.5 | 2:1 | 1 | 1:2 | 1:4 | 1:8 | 1:16 | 1:32 | 1:64 |
| | 6.25 | 4:1 | 2:1 | 1 | 1:2 | 1:4 | 1:8 | 1:16 | 1:32 |
| | 3.125 | 8:1 | 4:1 | 2:1 | 1 | 1:2 | 1:4 | 1:8 | 1:16 |
| | 1.56 | 16:1 | 8:1 | 4:1 | 2:1 | 1 | 1:2 | 1:4 | 1:8 |
| | 0.781 | 32:1 | 16:1 | 8:1 | 4:1 | 2:1 | 1 | 1:2 | 1:4 |
| | 0.391 | 64:1 | 32:1 | 16:1 | 8:1 | 4:1 | 2:1 | 1 | 1:2 |
| | 0.195 | 128:1 | 64:1 | 32:1 | 16:1 | 8:1 | 4:1 | 2:1 | 1:1 |

Controls (not shown) contain the medium with no biocide added.

Immediately after the microtiter plates are prepared, the optical density (OD) readings for each well is measured at 580 nm and the plates are then incubated at 37° C. for 24 hr. After the incubation period, the plates are gently agitated before $OD_{580}$ values are collected. The $OD_{580}$ values at $T_0$ are subtracted from $T_{24}$ values to determine the total amount of growth (or lack thereof) that occurs. These values are used to calculate the percent inhibition of growth caused by the presence of each biocide and each of the 64 combinations. A 90% inhibition of growth ($I_{90}$) value is used as a threshold for calculating synergy index (SI) values with the following equation:

$$\text{Synergy Index} = M_{DBMAL}/C_{DBMAL} + M_B/C_B$$

where $C_{DBMAL}$: Concentration of DBMAL required to inhibit at least 90% of bacterial growth when used alone
$C_B$: Concentration of biocide (B) required to inhibit at least 90% of bacterial growth when used alone.
$M_{DBMAL}$: Concentration of DBMAL required to inhibit at least 90% of bacterial growth when used in combination with biocide (B).
$M_B$: Concentration of biocide (B) required to inhibit at least 90% of bacterial growth when used in combination with DBMAL The SI values are interpreted as follows:
SI<1: Synergistic combination
SI=1: Additive combination
SI>1: Antagonistic combination In the Examples below, the amounts of biocides in the solution are measured in mg per liter of solution (mg/l). Since solution densities are approximately 1.00, the mg/l measurement corresponds to weight and can be expressed as parts per million (ppm). Both units may therefore be used interchangeably in the Examples.

Silver (Ag) and copper (Cu) are evaluated. For each metal, two separate experiments are carried out to determine if synergy can be detected when used in combination with DBMAL. Results of the experiments are presented in the following sections.

Example 1

DBMAL and Silver
Experiment 1

Although the Ag is added to the cell suspensions as $AgNO_3$, the indicated concentrations are for Ag in mg/l. DBMAL and Ag are tested individually and in selected ratios from 1:64 to 64:1 (DBMAL to Ag). The $I_{90}$ values for DBMAL and Ag are 12.5 mg/l and 0.063 mg/l, respectively. In the subsequent experiment, the $I_{90}$ value for Ag is 0.125 ppm. Regardless, in both studies, several synergistic combinations were detected. Table 2 contains ratios and synergy index values for the synergistic combinations

TABLE 2

| DBMAL (mg/l) | Ag (mg/l) | SI | Ratio (DBMAL:Ag) |
|---|---|---|---|
| 6.25 | 0.0156 | 0.75 | 400:1 |
| 6.25 | 0.0078 | 0.63 | 800:1 |
| 3.13 | 0.0313 | 0.75 | 100:1 |
| 3.13 | 0.0156 | 0.50 | 200:1 |
| 3.13 | 0.0078 | 0.37 | 400:1 |
| 1.56 | 0.0313 | 0.62 | 50:1 |
| 1.56 | 0.0156 | 0.38 | 100:1 |
| 1.56 | 0.0078 | 0.25 | 200:1 |
| 0.78 | 0.0313 | 0.55 | 25:1 |
| 0.78 | 0.0156 | 0.32 | 50:1 |
| 0.39 | 0.0313 | 0.52 | 12.5:1 |

As can be seen from the Table, a wide range of ratios of the two actives exhibit SI values <1, indicating a synergistic effect.

Experiment 2

As illustrated in Table 3, the results presented in Table 2 (Experiment 1) are reproducible and show a pattern of inhibition that is very similar to that obtained in Experiment 1.

TABLE 3

| DBMAL (mg/l) | Ag (mg/l) | SI | Ratio (DBMAL:Ag) |
|---|---|---|---|
| 6.25 | 0.0313 | 0.75 | 200:1 |
| 6.25 | 0.0156 | 0.63 | 400:1 |
| 3.125 | 0.0625 | 0.75 | 50:1 |
| 3.125 | 0.0313 | 0.50 | 100:1 |
| 3.125 | 0.0156 | 0.38 | 200:1 |
| 3.125 | 0.0078 | 0.31 | 400:1 |
| 1.563 | 0.0625 | 0.63 | 200:1 |
| 1.563 | 0.0313 | 0.37 | 50:1 |
| 1.563 | 0.0156 | 0.25 | 100:1 |
| 1.563 | 0.0078 | 0.19 | 200:1 |
| 0.781 | 0.0625 | 0.57 | 12.5:1 |
| 0.781 | 0.0313 | 0.31 | 25:1 |
| 0.391 | 0.0625 | 0.54 | 6.25:1 |
| 0.391 | 0.0313 | 0.28 | 12.5:1 |

Example 2

DBMAL and Copper

Table 6 shows inhibition growth assay results for DBMAL, Cu, and combinations thereof. 0.78 mg/l Cu is required for at least 90% inhibition of growth of the test organisms and, as previously detected, 12.5 mg/l DBMAL is needed to achieve the same effect. In the presence of some concentrations of the two actives that are less than the $I_{90}$ concentrations, the effect is observed to be synergistic. Data is shown in Table 4.

TABLE 4

| DBMAL (mg/l) | Cu (mg/l) | SI | Ratio (DBMAL:Cu) |
|---|---|---|---|
| 6.25 | 0.195 | 0.75 | 32:1 |
| 3.125 | 0.39 | 0.752 | 8:1 |
| 3.125 | 0.195 | 0.50 | 16:1 |
| 1.563 | 0.39 | 0.62 | 4:1 |
| 1.563 | 0.195 | 0.37 | 8:1 |
| 0.780 | 0.39 | 0.56 | 2:1 |
| 0.780 | 0.195 | 0.31 | 4:1 |
| 0.391 | 0.391 | 0.53 | 1:1 |
| 0.391 | 0.195 | 0.28 | 2:1 |

Experiment 2

In this experiment, similar results to Experiment 1 are obtained (see Table 5).

TABLE 5

| DBMAL (mg/l) | Cu (mg/l) | SI | Ratio (DBMAL:Cu) |
|---|---|---|---|
| 6.25 | 0.20 | 0.75 | 32:1 |
| 3.13 | 0.39 | 0.75 | 8:1 |
| 3.13 | 0.20 | 0.50 | 16:1 |
| 1.56 | 0.39 | 0.62 | 4:1 |
| 1.56 | 0.20 | 0.37 | 8:1 |
| 0.78 | 0.39 | 0.56 | 2:1 |
| 0.78 | 0.20 | 0.31 | 4:1 |

Example 3

Table 10 shows results of assays on DBMAL and zinc (Zn). No synergy was detected between these materials.

| DBMAL Alone | | Zn Alone | | DBMAL | Zn (mg/l) | | | | | | |
| mg/l | % Inhibition of Growth | mg/l | % Inhibition of Growth | mg/l | 2500.0 | 1250.0 | 625.0 | 312.5 | 156.2 | 78.1 | 39.0 | 19.5 |
|---|---|---|---|---|---|---|---|---|---|---|---|---|
| 25.00 | 100 | 2500.0 | 92 | 25.00 | 100 | 100 | 100 | 84 | 87 | 100 | 100 | 100 |
| 12.50 | 100 | 1250.0 | 91 | 12.50 | 67 | 100 | 100 | 84 | 94 | 100 | 95 | 100 |
| 6.25 | 29 | 625.0 | 74 | 6.25 | 80 | 80 | 74 | 89 | 55 | 25 | 15 | 0 |
| 3.13 | 21 | 312.5 | 33 | 3.13 | 88 | 67 | 72 | 44 | 24 | 22 | 7 | 0 |
| 1.56 | 9 | 156.3 | 23 | 1.56 | 85 | 89 | 68 | 8 | 0 | 23 | 0 | 0 |
| 0.78 | 4 | 78.1 | 18 | 0.78 | 85 | 61 | 85 | 17 | 2 | 0 | 0 | 0 |
| 0.39 | 0 | 39.1 | 12 | 0.39 | 87 | 76 | 79 | 0 | 0 | 0 | 0 | 0 |
| 0.20 | 2 | 19.5 | 19 | 0.20 | 97 | 81 | 67 | 0 | 0 | 0 | 0 | 0 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A synergistic biocidal composition comprising 2,2-dibromomalonamide and silver wherein the weight ratio of 2,2-dibromomalonamide to the silver is 800:1 to 1:1.

2. The composition according to claim 1 wherein the silver is provided from an inorganic or organic source selected from: silver acetate, silver acetylacetonate, silver arsenate, silver benzoate, silver bromate, silver bromide, silver carbonate, silver chlorate, silver chloride, silver chromate, silver citrate hydrate, silver cyanate, silver cyclohexanebutyrate, silver fluoride, silver heptafluorobutyrate, silver hexafluoroantimonate, silver hexafluoroarsenate, silver hexafluorophosphate, silver hydrogen fluoride, silver iodate, silver iodide, silver lactate, silver metavanadate, silver methanesulfonate, silver methenamine, silver molybdate, silver nitrate, silver nitrite, silver oxide, silver pentafluoropropionate, silver perchlorate hydrate, silver perchlorate monohydrate, silver perchlorate, silver phosphate, silver phthalocyanine, silver picolinate, silver protein, silver proteinate, silver p-toluenesulfonate, silver selenide, silver sulfadiazine, silver sulfate, silver sulfide, silver sulfite, silver telluride, silver tetrafluoroborate, silver thiocyanate, silver trifluoroacetate, silver trifluoromethanesulfonate, and silver tungstate.

3. The composition according to claim 1 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration systems, swimming pool or spa water.

4. A method for controlling microorganism growth in an aqueous or water-containing system, the method comprising treating the aqueous or water-containing system with an effective amount of a composition according to claim 1.

5. The method according to claim 4 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration system, swimming pool or spa water.

6. A synergistic biocidal composition comprising 2,2-dibromomalonamide and copper wherein the weight ratio of 2,2-dibromomalonamide to the copper is 32:1 to 1:1, further wherein the copper is provided from an inorganic or organic source selected from: copper acetylacetonate; copper bromide; copper carbonate; copper chloride; copper chromite; copper cyanide; copper cyclohexanebutyrate; copper D-gluconate; copper fluoride; copper formate hydrate; copper hexafluoroacetylacetonate hydrate; copper hydroxide; copper iodide; copper iodide dimethyl sulfide complex; copper iodide trimethylphosphite complex; copper methoxide; copper molybdate; copper nitrate; copper oxide; copper oxychloride; copper perchlorate hexahydrate; copper pyrophosphate hydrate; copper selenide; copper selenite; copper sulfate; copper sulfide; copper tartrate hydrate; copper telluride; copper thiocyanate; copper thiophene-2-carboxylate; copper thiophenolate; copper trifluoroacetylacetonate; copper 1-butanethiolate; copper 2-ethylhexanoate; copper 3-methylsalicylate; or copper trifluoromethanesulfonate.

7. The composition according to claim 6 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration systems, swimming pool or spa water.

8. A method for controlling microorganism growth in an aqueous or water-containing system, the method comprising treating the aqueous or water-containing system with an effective amount of a composition according to claim 6.

9. The method according to claim 8 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration system, swimming pool or spa water.

* * * * *